US007260249B2

(12) United States Patent
Smith

(10) Patent No.: US 7,260,249 B2
(45) Date of Patent: Aug. 21, 2007

(54) RULES-BASED APPROACH FOR PROCESSING MEDICAL IMAGES

(75) Inventor: Justin P. Smith, Hunts Point, WA (US)

(73) Assignee: Confirma Incorporated, Kirkland, WA (US)

( * ) Notice: Subject to any disclaimer, the term of this patent is extended or adjusted under 35 U.S.C. 154(b) by 906 days.

(21) Appl. No.: 10/260,735

(22) Filed: Sep. 27, 2002

(65) Prior Publication Data

US 2004/0064037 A1   Apr. 1, 2004

(51) Int. Cl.
*G06K 9/00* (2006.01)
(52) U.S. Cl. .......................... 382/128; 382/274; 378/28
(58) Field of Classification Search ................ 382/128, 382/129, 130, 131, 132, 133, 162, 168, 169, 382/203, 209, 232, 255, 274, 291, 305; 345/420; 378/37, 28, 62; 324/309, 307; 600/408
See application file for complete search history.

(56) References Cited

U.S. PATENT DOCUMENTS

| 4,839,805 | A |   | 6/1989  | Pearson, Jr. et al. .... 364/413.14 |
|-----------|---|---|---------|-------------------------------------|
| 5,262,945 | A |   | 11/1993 | DeCarli et al. ........ 364/413.13   |
| 5,311,131 | A |   | 5/1994  | Smith ..................... 324/309   |
| 5,627,907 | A | * | 5/1997  | Gur et al. ................ 382/132   |
| 5,638,465 | A |   | 6/1997  | Sano et al. ............... 382/281   |
| 5,644,232 | A |   | 7/1997  | Smith ..................... 324/309   |
| 5,768,333 | A | * | 6/1998  | Abdel-Mottaleb ........... 378/37    |
| 5,818,231 | A |   | 10/1998 | Smith ..................... 324/309   |
| 5,920,319 | A | * | 7/1999  | Vining et al. ............. 345/420   |
| 6,240,201 | B1| * | 5/2001  | Xu et al. .................. 382/130   |
| 6,310,477 | B1| * | 10/2001 | Schneider ................. 324/307   |

(Continued)

FOREIGN PATENT DOCUMENTS

JP   8 69533 A   3/1996

(Continued)

OTHER PUBLICATIONS

Dasarathy, "Is Your Nearest Neighbor Near Enough a Neighbor?" in *Proceedings of the First International Conference on Information Sciences and Systems*, Patras, Greece, 1976, pp. 114-117.

(Continued)

*Primary Examiner*—Matthew C. Bella
*Assistant Examiner*—Seyed Azarian
(74) *Attorney, Agent, or Firm*—Michael J. Donohue; David Wright Tremaine LLP

(57) ABSTRACT

A technique flexibly applies pre-programmed rules that specify the manner in which medical image data is to be classified or otherwise processed. A rules-based system selects from the pre-programmed rules, with different rules being used based on different doctors' preferences, such as during contrast agent studies. The rules-based system is initially "taught" how to apply a doctor's rules via a sample data image set, and then automatically applies the same rules to that doctor's image data whenever that image data is subsequently provided, thereby avoiding the need for doctors to constantly reconfigure a system with their own rules repetitively for each and every image or to otherwise place the burden of processing on the doctor. The programmed rules can include rules from the available literature—the doctors or other users are free to select from these available rules, modify/customize them to generate new rules, or provide completely new rules.

41 Claims, 8 Drawing Sheets

U.S. PATENT DOCUMENTS

| | | | |
|---|---|---|---|
| 6,317,617 B1 * | 11/2001 | Gilhuijs et al. | 600/408 |
| 6,687,329 B1 * | 2/2004 | Hsieh et al. | 378/62 |
| 6,771,822 B1 * | 8/2004 | Brackett | 382/232 |
| 6,956,373 B1 * | 10/2005 | Brown et al. | 324/309 |

FOREIGN PATENT DOCUMENTS

| | | |
|---|---|---|
| WO | WO 01/57777 A2 | 8/2001 |

OTHER PUBLICATIONS

Bezdek, et al., "FCM: The Fuzzy c-Means Clustering Algorithm," *Computer & Geosciences*, 10(2-3):191-203, 1984.

Vannier et al., "Multispectral Analysis of Magnetic Resonance Images," *Radiology*, 154(1):221-224, 1985.

Xie et al., "A Validity Measure for Fuzzy Clustering," *IEEE Transactions on Pattern Analysis and Machine Intelligence*, 13(8):841-847, 1991.

Clarke et al., "Comparison of Supervised Pattern Recognition Techniques and Unsupervised Methods for MRI Segmentation," *Medical Imaging VI: Image Processing*, 1652:668-677, 1992.

Taxt et al., "Multispectral Analysis of Uterine Corpus Tumors in Magnetic Resonance Imaging," *Magnetic Resonance in Medicine*, 23:55-76, 1992.

Bezdek et al., "Review of MR Image Segmentation Techniques Using Pattern Recognition," *Medical Physics*, 20(4):1033-1048, 1993.

Taxt et al., "Multispectral Analysis of the Brain Using Magnetic Resonance Imaging," *IEEE Transactions on Medical Imaging*, 13(3):470-481, 1994.

Clarke et al., "MRI Segmentation: Methods and Applications," *Magnetic Resonance Imaging*, 13(3):343-368, 1995.

Dasarathy "Adaptive Decision Systems with Extended Learning for Deployment in Partially Exposed Environments," *Optical Engineering*, 34(5):1269-1280, 1995.

Pham et al., "Partial Volume Estimation and the Fuzzy C-means Algorithm," 4 pages.

Mussurakis et al., "Dynamic MRI of Invasive Breast Cancer: Assessment of Three Region-of-Interest Analysis Methods." *Journal of Computer Assisted Tomography*, 21(3):431-438, 1997.

Samarasekera et al., "A New Computer-Assisted Method for the Quantification of Enhancing Lesions in Multiple Sclerosis," *Journal of Computer Assisted Tomography*, 21(1):145-151, 1997.

"Spatial Filtering," Digital Image Processing 4.3, pp. 189-195.

Clark et al., "Automatic Tumor Segmentation Using Knowledge-Based Techniques," *IEEE Transactions on Medical Imaging*, 17(2):187-201, 1998.

Clark et al., "MRI Measurement of Brain Tumor Response: Comparison of Visual Metric and Automatic Segmentation," *Magnetic Resonance Imaging*, 16(3):271-279, 1998.

Houben et al., "Distance Rejection in the Context of Electric Power System Security Assessment Based on Automatic Learning," in *Proceedings of Advances in Pattern Recognition: Joint IAPR International Workshops SSPR '98 and SPR '98*, Sydney, Australia, 1998, pp. 756-764.

Parker et al., "MRIW: Parametric Analysis Software for Contrast-Enhanced Dynamic MR Imaging in Cancer," *RadioGraphics*, 18(2):497-506, 1998.

Reiss et al., "Reliability and Validity of an Algorithm for Fuzzy Tissue Segmentation of MRI," *Journal of Computer Assisted Tomography*, 22(3):471-479, 1998.

Weinstein et al., "Breast Fibroadenoma: Mapping of Pathophysiologic Features with Three-Time-Point, Contrast-Enhanced MR Imaging—Pilot Study," *Radiology*, 210(1):233-240, 1999.

Kuhl et al., "Dynamic Breast MR Imaging: Are Signal Intensity Time Course Data Useful for Differential Diagnosis of Enhancing Lesions?," *Radiology*, 211(1):101-110, 1999.

Orel, "Differentiating Benign from Malignant Enhancing Lesions Identified at MRI Imaging of the Breast: Are Time-Signal Intensity Curves an Accurate Predictor?," *Radiology*, 211(1):5-7, 1999.

Liney et al., "Dynamic Contrast-Enhanced MRI in the Differentiation of Breast Tumors: User-Defined Versus Semi-Automated Region-of-Interest Analysis," *Journal of Magnetic Resonance Imaging* 10:945-949, 1999.

Hylton, "Vascularity Assessment of Breast Lesions with Gadolinium-Enhanced MR Imaging," *MRI Clinics of North America*, 9(2):321-331, 2001.

Hylton, "Vascularity Assessment of Breast Lesions with Gandolinium-Enhanced MR Imaging," *MRI Clinics of North America* 7(2):411-420, May 1999.

* cited by examiner

```
                 DOCTOR X RULES: HOSPITAL W: CONTRAST
      ⎧   PRECONTRAST SERIES:    3
   68 ⎨
      ⎩   PRECONTRAST SERIES:    4

⎧   SUBTRACTION SERIES:    #4-#1
   70 ⎨
      ⎩                          #5-#2

⎧   UPTAKE RATE:           85% ± 3%
      ⎪
   72 ⎨   UPTAKE INTERVAL:       1.1 min ± 0.5 min
      ⎪
      ⎩   WASHOUT RATE:          7% ± 2%

⎧   MALIGNANT:             RED
   74 ⎨
      ⎩   SUSPECT:               BLUE

76 ⎰   LINK ALIGNED SLICES:   SERIES #1-#5
      ⎱              ⋮
```

*Fig. 5*

```
                       DOCTOR X
                       BASELINE DATA

⎧   PATIENT ID:    127A
   78 ⎨
      ⎩                  136B

⎧   SAMPLE IMAGE/SERIES:       7/8
   80 ⎨
      ⎩                              12/3

⎧   MALIGNANT:     80-100
   82 ⎨   SUSPECT:       60-79
      ⎩   NORMAL:        0-59
                     ⋮
```

RULES-BASED APPROACH FOR PROCESSING MEDICAL IMAGES

TECHNICAL FIELD

This disclosure generally relates to processing of image data, and in particular but not exclusively, relates to a flexible rules-based approach for processing medical images.

BACKGROUND INFORMATION

The collection and storage of a large number of medical images is currently carried out by a number of systems. The medical images can be collected by a variety of techniques, such as nuclear magnetic resonance (NMR), magnetic resonance imaging (MRI), computed tomography (CT), ultrasound, and x-rays. One system for collecting a large number of medical images of a human body is disclosed U.S. Pat. Nos. 5,311,131 and 5,818,231 to Smith. These patents describe an MRI apparatus and method for collecting a large number of medical images in various data sets. The data are organized and manipulated in order to provide visual images to be read by medical personnel to perform a diagnosis.

One of the problems in reading a large number of images is for the medical personnel to understand the relationship of the images to each other while performing the reading. Another difficult task is interpreting the medical significance of various features that are shown in the individual images. Being able to correlate the images with respect to each other is extremely important in deriving the most accurate medical diagnosis from the images and in setting forth a standard of treatment for the respective patient. Unfortunately, such a coordination of multiple images with respect to each other is extremely difficult and even highly trained medical personnel, such as experienced radiologists, have extreme difficulty in consistently and properly interpreting a series of medical images so that a treatment regime can be instituted that best fits the patient's current medical condition.

Another problem encountered by medical personnel today is the large amount of data and numerous images that are obtained from current medical imaging devices. The number of images collected in a standard scan is usually in excess of 100 and very frequently numbers in the many hundreds. In order for medical personnel to properly review each image takes a great deal of time, and with the many images that current medical technology provides, a great amount of time is required to thoroughly examine all the data.

These problems are compounded by the fact that there is a wide variety of literature and research that provide different approaches as to how to analyze the data. Different doctors use different analytical criteria to determine whether tissue shown in images is malignant or benign, for instance. Indeed, it is universally accepted that doctors will often have different opinions as to the diagnosis and treatment regimen for a particular patient. Hence, patients often obtain "second opinions" as a means for comparing doctors' diagnosis and suggested treatment regimens.

However, despite the large amount of available data and despite the fact that doctors often take different evaluative approaches, existing technology has not been able to adapt to these environments. For example, when generating and displaying images for a doctor to review, the imaging device (sometimes referred to as a "workstation") uses a standard set of configuration settings to sort, classify, or otherwise process the images. The configuration settings are applied universally to all patients and to all images.

While this uniformity of processing provides simplicity, it is non-ideal. Human tissue behavior will vary greatly (or subtly) from one patient to another during the image acquisition process. Moreover, diseases will often act differently on different types of tissue, thereby producing differences in images. Thus, if certain analytical criteria is used to classify tissue images of a particular patient and is suggestive of the presence of cancerous tissue, that conclusion may not necessarily apply to tissue of another patient that is processed using the same analytical criteria. Misdiagnosis may result.

Moreover, using a standard set of parameters to universally process all images forces doctors to conform their analysis and conclusions to be consistent with the standard parameters. This can result in misdiagnosis, particularly if a certain patient has a tissue condition that is inconsistent with tissue behavior on which the standard parameters are based. Alternatively, doctors may be forced to constantly adjust their individual independent analysis to account for the standardization of the images. This can create a certain amount of guesswork and approximation that ultimately may be detrimental to the patient.

A possible solution may be to allow doctors to perform adjustments to the preset criteria via the workstation. However, some doctors are not as computer-savvy as other doctors, and requiring doctors to repeatedly perform this reconfiguration of settings for all images, each and every time they log onto a workstation, is too burdensome of a task to be beneficial.

BRIEF DESCRIPTION OF THE SEVERAL VIEWS OF THE DRAWINGS

FIG. 5 shows example rules that can be used by an embodiment of the invention.

FIG. 6 shows example baseline data that can be used by an embodiment of the invention.

DETAILED DESCRIPTION

Figure 1:
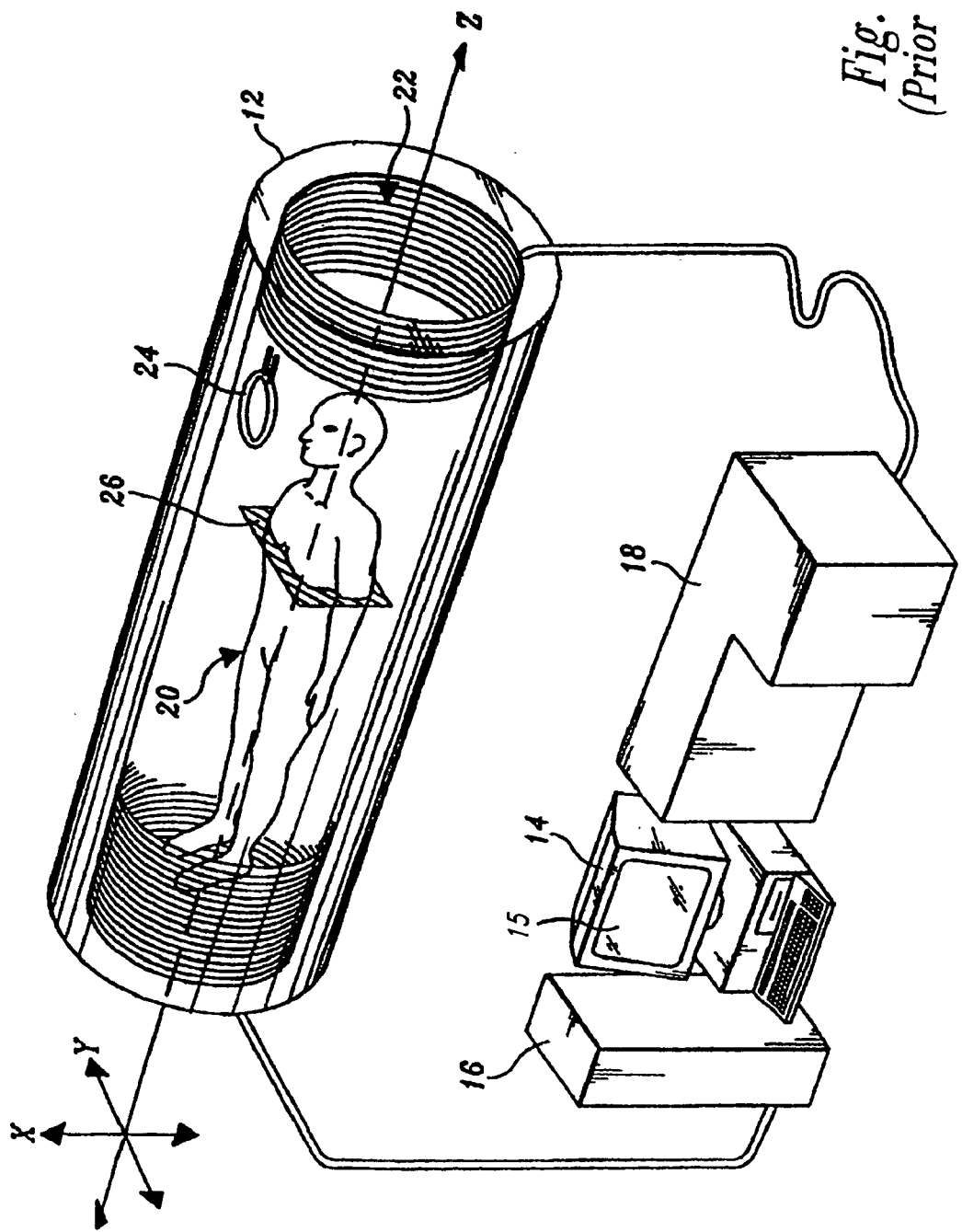
FIG. 1 is a schematic view of a data collection system according to the prior art.

Embodiments of a rules-based approach for processing images, such as medical images, are described herein. In the following description, numerous specific details are given to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail, as they will be understood by those skill in the art.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

According to one embodiment of the present invention, a medical image is provided for review by a physician, such as a radiologist. Under a computer command issued by the radiologist, the underlying data that created the medical image is compared to a set of rules that screen for a potential disease tissue, such as cancerous tissue. The data is compared to a preset data table, and a search is made for data that falls within the criteria of the rules set forth in the table. After the comparison is completed, the image displayed to the doctor is enhanced by marking an indication of that portion of the medical image that corresponds to the data matching the rules found in the table. This indication provides a highlight to the physician so that he may examine the data in more detail to determine whether or not this particular tissue is disease tissue, such as a malignant tumor. The physician thus has his attention directed towards any portion of the image for which the underlying data indicates a likelihood of a disease for which the radiologist is screening.

The physician has the flexibility to input the rules into the table to customize the system to look for the same disease using different rules or, alternatively, to look for different diseases. For example, the physician may input a separate set of rules based on recent medical findings to locate cancerous tissue using principles unavailable at the time the program was originally written. Alternatively, the data may have stored into it two or three different sets of rules for looking at breast cancer, and two or three different sets of rules for locating brain cancer, thus refining the physician's approach for locating different types of cancer in different parts of the body. Alternatively, the rules therein may be based on a different disease or ailment other than cancer. The rules may be based to enhance the location of nerve cells, to identify various diseases of the nervous system. Alternatively, the rules stored in the table may enhance certain portions of a body organ, such as the liver tissue subject to different diseases, such as scoliosis or hepatitis, thus permitting the physician to focus quickly on whether or not such disease are present in different tissues throughout the human body.

As an overview, one embodiment of the invention provides a technique to flexibly apply one or more available rules that specify the manner in which data within a medical image is to be classified or otherwise processed. For example, medical images of tissue taken at intervals of time after a contrast agent is injected have pixel intensity changes that are often indicative of healthy or unhealthy tissue. A rules-based system of an embodiment of the invention may be pre-programmed with a plurality of rules from which to select. One set of rules for a first doctor may be to highlight in red color pixels that represent tissue having an 80% enhancement during the first (1.0) minute of uptake and having a subsequent 5% washout, as an illustrative example. A second set of rules for a second doctor may be slightly (or greatly) different (e.g., 90% enhancement during the first 1.3 minutes of uptake and 5.8% washout, highlighted in green color).

The rules-based system selects the appropriate rule to use based on the preferences of the doctor (or based on some other criteria that specify the manner in which the rules are to be selected), and applies the same selected rule to that doctor's image data whenever that doctor's image data is provided. Thus, each doctor can potentially have their image data processed in a manner different than the other doctors, if desired.

According to one embodiment, the rules-based system is initially "taught" how to apply the rules. That is, the rules-based system is programmed with the plurality of rules, and is then given a sample image data set and instructed to apply a selected rule to that sample image data set. Whenever similar future image data sets are provided in the future to the rules-based system from image acquisition devices, the rules-based system thus knows which rule(s) to apply to the similar image data sets and automatically processes the image data sets accordingly, thereby avoiding the need for doctors to constantly reconfigure a system with their own rules repetitively for each and every image or to otherwise place the burden of processing at the doctor's end.

In one embodiment, the programmed rules include rules from the available literature. These are stored in the table and the physician can select to use the main set of rules, or a second set of rules. Alternatively, as new rules are medically validated during ongoing research, such rules can be programmed into the rules-based system. The doctors or other users are free to select from these available rules, modify/customize them to generate new rules, or provide completely new rules. The rules can be in any suitable format, including mathematical formulas, logical rules, minimum and maximum thresholds, and others and combinations thereof that would be familiar to those skilled in the art having the benefit of this disclosure. One embodiment of the rules-based invention may also be used to test or validate proposed rules.

For purposes of explanation and illustration, embodiments of the invention will be described herein in the context of magnetic resonance imaging (MRI) and related analysis. One embodiment of the invention has application in contrast studies, where a contrast agent is applied to the tissues of the patient in order to provide enhanced images that depict tissue behavior during "uptake" and "washout" of the contrast agent. It is appreciated that the invention is not limited to MRI or contrast studies, and that other embodiments of the invention may be applied to other medical imaging technologies, including but not limited to, nuclear magnetic resonance (NMR), computed tomography (CT), positron emission tomography (PET), ultrasound, x-rays, and other imaging technique. Some embodiments of the invention may also be used in connection with imaging technologies that are not necessarily medical in nature.

Beginning initially with FIG. 1, shown therein is a known sensor and data collection device as described in U.S. Pat. No. 5,644,232. It illustrates one technique by which data can be collected for analysis for use by one embodiment of the present invention.

Details of magnetic resonance imaging methods are disclosed in U.S. Pat. No. 5,311,131, entitled, "MAGNETIC RESONANCE IMAGING USING PATTERN RECOGNITION;" U.S. Pat. No. 5,644,232, entitled, "QUANTITATION AND STANDARDIZATION OF MAGNETIC RESONANCE MEASUREMENTS;" and U.S. Pat. No. 5,818,231, entitled, "QUANTITATION AND STANDARDIZATION OF MAGNETIC RESONANCE MEASUREMENTS." The above-referenced three patents are incorporated in their entirety herein by reference. The technical descriptions in these three patents provide a background explanation of one environment for the invention and are beneficial to understand the present invention.

Pattern recognition is utilized in several disciplines and the application of thresholding as described with respect to this invention is pertinent to all of these fields. Without the loss of generality, the examples and descriptions will all be limited to the field of MRI for simplicity. Of particular interest is the application of pattern recognition technology in the detection of similar lesions such as tumors within magnetic resonance images. Therefore, additional background on the process of MRI and the detection of tumor using MRI is beneficial to understanding embodiments of the invention.

Magnetic resonance (MR) is a widespread analytical method used routinely in chemistry, physics, biology, and medicine. Nuclear magnetic resonance (NMR) is a chemical analytical technique that is routinely used to determine chemical structure and purity. In NMR, a single sample is loaded into the instrument and a representative, multivariate, chemical spectrum is obtained. The magnetic resonance method has evolved from being only a chemical/physical spectral investigational tool to an imaging technique, MRI, that can be used to evaluate complex biological processes in cells, isolated organs, and living systems in a non-invasive way. In MRI, sample data are represented by an individual picture element, called a pixel, and there are multiple samples within a given image, or other diseases in the tissue.

Magnetic resonance imaging utilizes a strong magnetic field for the imaging of matter in a specimen. MRI is used extensively in the medical field for the noninvasive evaluation of internal organs and tissues, including locating and identifying benign or malignant tumors.

As shown in FIG. 1, a patient 20 is typically placed within a housing 12 having an MR scanner, which is a large, circular magnet 22 with an internal bore large enough to receive the patient. The magnet 22 creates a static magnetic field along the longitudinal axis of the patient's body 20. The magnetic field results in the precession or spinning of charged elements such as the protons. The spinning protons in the patient's tissues preferentially align themselves along the direction of the static magnetic field. A radio frequency electromagnetic pulse is applied, creating a new temporary magnetic field. The proton spins now preferentially align in the direction of the new temporary magnetic field. When the temporary magnetic field is removed, the proton spin returns to align with the static magnetic field. Movement of the protons produces a signal that is detected by an antenna 24 associated with the scanner. Using additional magnetic gradients, the positional information can be retrieved and the intensity of the signals produced by the protons can be reconstructed into a two- or three-dimensional image.

The realignment of the protons' spin with the original static magnetic field (referred to as "relaxation") is measured along two axes. More particularly, the protons undergo a longitudinal relaxation ($T_1$) and transverse relaxation ($T_2$). Because different tissues undergo different rates of relaxation, the differences create the contrast between different internal structures, as well as a contrast between normal and abnormal tissue. In addition to series of images composed of $T_1$, $T_2$, and proton density, variations in the sequence selection permit the measurement of chemical shift, proton bulk motion, diffusion coefficients, and magnetic susceptibility using MR. The information obtained for the computer guided tissue segmentation may also include respective series that measure such features as: a spin-echo (SE) sequence; two fast spin-echo (FSE) double echo sequences; and fast short inversion time inversion recovery (FSTIR), or any of a variety of sequences approved for safe use on the imager. Further discussion of $T_1$-weighted and $T_1$-weighted images and the other types of images identified above (and various techniques to interpret these images) are provided in the co-pending application(s) referenced herein and in the available literature, and are not repeated herein for purposes of brevity.

Contrast agents are types of chemicals that may be administered to the subject during an MRI or other medical examination. Generally, a contrast agent is prepared for injection into a blood vessel of the patient prior to the study. A first set of images is created before the contrast agent is injected, at time $t_1$. At a second point in time, $t_2$, the contrast agent is injected. The time at which the contrast agent is injected is carefully tracked and additional sets of images are created at selected time intervals. For example, a second set of images can be created at time $t_3$, which will then be compared to the images taken at time $t_1$. Further, sets of images can be obtained at additional times, such as at $t_4$, $t_5$, $5_6$, etc. Commonly, the different sets of images are obtained at set intervals following the injection of the contrast agent at time $t_2$, such as every 90 seconds, every 180 seconds, or the like. The physician may decide to obtain one or many post-contrast agent image sets. Contrast agents typically distribute in various tissues of the body over time and provide some degree of enhanced image for interpretation by the user of certain attributes of the tissues based on the contrast agent distribution through the tissue. In addition to the above, pre- and post-contrast sequence data series can be acquired. When the contrast agents distribute in various tissues of the body over time, the images generated from tissues that have absorbed the contrast agents will have different pixel intensities. The pixel intensities, the rates at which the contrast agents are absorbed by tissue (during "uptake"), the rates at which the pixel intensities decrease (as the contrast agents "washout"), and other characteristics vary from one patient to another and from one type of tissue to another. As an example, fatty tissue has different uptake and washout rates than malignant tissue. Healthy muscle tissue has different uptake and washout rates than fatty tissue and malignant tissue. Studies have shown that malignant tissue tends to have more rapid uptake rates and more rapid washout rates, as compared to other types of tissue, for instance. A more detailed discussion of these subjects may be found in the available literature and would be familiar to those skilled in the art having the benefit of this disclosure. For the sake of brevity, such detailed discussion is omitted herein.

Contrast agents are described in Christiane K. Kuhl et al., "DYNAMIC BREAST MR IMAGING: ARE SIGNAL INTENSITY TIME COURSE DATA USEFUL FOR DIFFERENTIAL DIAGNOSIS OF ENHANCING LESIONS?," Radiology, vol. 211, No. 1, April 1999, pp. 101-110; and in Nola M. Hylton, "VASCULARITY ASSESSMENT OF BREAST LESIONS WITH GADOLINIUM-ENHANCED MR IMAGING," MRI Clinics of North America, vol. 9, No. 2, May 2002, pp. 321-331, with both of these articles being incorporated herein by reference in their entirety.

When displayed as an image, the collected data can be represented as data points in the image, such as pixels, voxels, or any other suitable representation. Within a visual display, the intensity, color, and other features of the respective pixel, provides an indication of the medical parameter of interest. (As used herein, the term "pixel" will be used in the broad, generic sense to include any individual component that makes up a visual image that is under examination and includes within the meaning such things as pixels, any data point representing two-dimensional data, voxels having three or more dimensional data, a grayscale data point or other visual component from an MRI image, NMR, CT, ultrasound, or other medical image). The medical image thus contains a large number of pixels each of which contain data corresponding to one or more medical parameters within a patient, an entire image being made up of a large number of pixels.

In FIG. 1, an object to be examined, in this case the patient's body 20, is shown. A slice 26 of the body 20 under examination is scanned and the data collected. The data are collected, organized and stored in a signal-processing module 18 under control of a computer 14. A display 15 may display the data as they are collected and stored. It may also provide an interface for the user to interact with and control the system. A power supply 16 provides power for the system.

Figure 2:
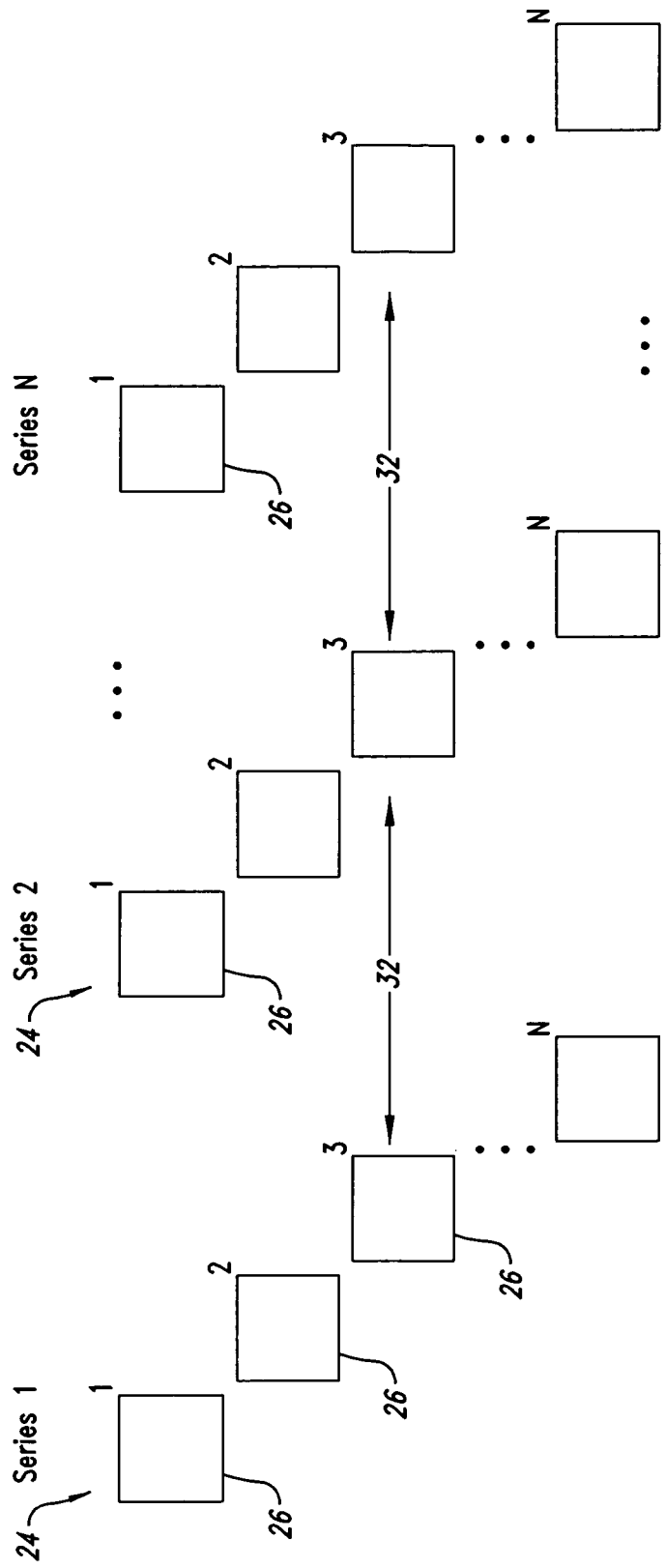
FIG. 2 is a schematic representation of various images that may be obtained from a data collection system.

FIG. 2 illustrates the image data that may be collected by the image acquisition device of FIG. 1 according to one embodiment of the present invention. The medical images that are obtained can be considered as being organized in a number of different series 24. Each series 24 is comprised of data that is collected by a single technique and at a selected time and its corresponding imager settings. For example, one series 24 may be made up of T1-weighted images. A second series 24 may be made up of T2-weighted images. A third series 24 may be made up of a spin echo sequence (SE). Another series 24 may be made up of a STIR or inversion recovery sequence.

In an alternative embodiment, each series is made using the same technique but at selected time intervals following the injection of a contrast agent. The first series is taken at time $t_1$ before the contrast agent is injected. At a selected time, $t_2$ the contrast agent is injected. The second series is then taken at time $t_3$ of the same location in the body, after the contrast agent has started to move into the tissue. Additional series can be taken if desired, at subsequent times to create N number of series taken at selected times $t_{N+1}$. In this way, hundreds of images can be collected, all of which need to be analyzed for the potential of containing useful data. A number of series may be obtained during the data collection process. It is typical to obtain between six and eight series 24 and in some instances, ten or more different series 24 of data for a single patient during a data collection scan. In some situations, the different series may have a temporal relationship relative to each other.

Each series 24 is comprised of a large number of images, each image representing a slice 26 within the medical body under examination. The slice 26 is a cross-sectional view of particular tissues within a plane of the medical body under interest. A second slice 26 is taken spaced a small distance away from the first slice 26. A third slice 26 is then taken spaced from the second slice. A number of slices 26 are taken in each series 24 for the study being conducted until N slices have been collected and stored. Under a normal diagnostic study, in the range of 25-35 spatially separated slices are collected within a single series. In other situations, 80-100 spatially separated slices are collected within a single series. Of course, in a detailed study, the number of slices 26 being obtained may be much higher for each series. For example, it may number in the hundreds in some examples, such as for a brain scan, when a large amount of data is desired, or a very large portion of the medical body is being tested.

Generally, each series 24 has the same number of slices, and further, a slice in each series is taken at the same location in the body as the corresponding slice in the other series. A slice set 32 is made up of one slice from each of the series taken at the same location within the medical body under study. For example, a group made of slice #3 from each of the series 24 would comprise a slice set 32 of aligned slices, assuming that all of the slices indexed as #3 are taken from the same spatial location within the body. Being able to assemble, classify or otherwise process, and understand the various data in a slice set 32 (and their relationship with one another) can be very valuable as a diagnostic tool.

If each series 24 has a certain number of slices, such as 30, and there are 6 to 8 series collected then the total number of images collected is in the range of 180 to 240 distinct and separate images. Just viewing each image individually is an extremely difficult, and burdensome task. Even if time permits that all the images can be all viewed, manually sorting them in a meaningful sequence and understanding the relationship among the various slices and various series is extremely difficult. Even though the image data may be stored in a database and the medical personnel may have access to a workstation for retrieving and viewing the images, the massive amount of information contained in the various images together with the huge number of images that are available make properly reading and understanding all of the data in the images a very time consuming and difficult task. During the time consuming and difficult nature of the task of viewing, comparing, and correlating all of the various images, the medical personnel may sometimes miss important diagnostic information within a particular image. If this diagnostic information is not properly viewed and interpreted as compared to the other images, errors may be made in understanding the patient's medical condition, which may result in errors related to the medical procedures and protocol used in caring for the patient.

Therefore, one embodiment of the present invention provides a rules-based system that can better assist medical personnel in their evaluation of this voluminous amount of image data. Once the image data is acquired by the image acquisition device of FIG. 1 and organized into series and slices as depicted in FIG. 2 (although organization into series and slices is not required), the acquired image data can be analyzed by the rules-based system and processed in accordance with the applicable rule or rules. The processing can include, but not be limited to, adding color to highlight tissues of interest, identifying with pixels from those images that exhibit certain threshold intensities and intensity changes within the rules, matching and sequencing images that share common characteristics regarding tissues of interest, locating and classifying images depicting tissue that exhibit certain behavior, generating new images (such as a subtraction series) from the received images, and others and combinations thereof.

Additional rules-based operations could include applying morphological operators, such as measures of statistical texture and fractal dimension or statistical complexity of the margins of various regions of tissue within the imaged region to one or more images in a slice set 32. Complex operations on the slice set 32 can be accomplished by creating compound rules that are comprised in whole or in part of rules that have already been created. For example, such a compound rule could specify that pixels identified by rule A, rule B, or rule C, and having the characteristics identified by rule D but not those characteristics identified by rule E be indicated by superimposing an "X" over them. Simple rules and compound rules can be combined using a variety of operators, including mathematical operators (e.g., addition, subtraction, division, multiplication, and others) and logical operators (e.g., AND, OR, NOT, AND NOT, NOR, IF, IF THEN, and others). These compound operations could be used, for example, to combine contrast enhancement measurements with morphologic measurements to create a new series that would indicate tissues (pixels) that would be of increased probability of possessing a certain characteristic, such as malignancy or infarction. Rules could also be constructed to incorporate data that was obtained from databases that would not be derived from the image set; for example, a rule might specify that IF a pixel shows greater than 80% enhancement in the first minute AND the patient is older younger than 50 years OR the patient's body mass index is greater than 30 AND the patient is in a defined high-risk population for breast cancer, THEN the pixel is to be indicated with a color.

Those pixels that match the rules may be highlighted with a selected color, and thus the image has a mark thereon to attract the attention of the medical personnel. If the tumor tissue is very small, such as occurs at the inception of cancer, even a trained radiologist may miss the tissue in a standard image. But, when processed as taught herein, the tissue which matches the rules is identified as being of interest and marked, such as by a different color other marking or text. This occurs even if only a very small number of pixels meet the rules standard. The attention of the radiologist is thus drawn quickly to this tissue for further study.

Figure 3:
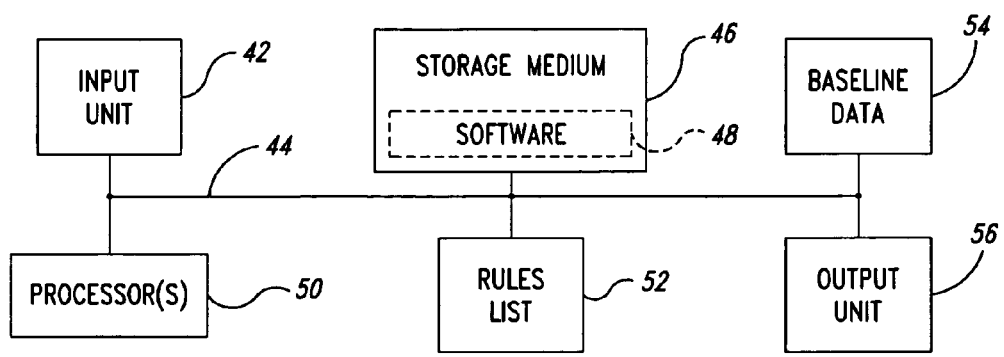
FIG. 3 is a block diagram of a rules-based system for processing images in accordance with an embodiment of the invention.

FIG. 3 is a block diagram of a rules-based system 40 for processing images in accordance with an embodiment of the invention. For simplicity of explanation, not all of the possible components of the system 40 are shown—only components relevant to understanding operation of the embodiment are depicted. Moreover, the various components and their associated operations may be integrated or otherwise combined, without necessarily having to be separate components. It is appreciated that the system 40 may be embodied in a discrete device, in a distributed system, or combination thereof. The system 40 may be implemented in a workstation (or other imaging device), personal computer (PC), or other suitable device. One example of an apparatus that can centrally implement the system 40 to pre-process images for remote terminals is disclosed in U.S. application Ser. No. 10/260,734, entitled "SYSTEM AND METHOD FOR DISTRIBUTING CENTRALLY LOCATED PRE-PROCESSED MEDICAL IMAGE DATA TO REMOTE TERMINALS," filed concurrently herewith, with inventors Chris H. Wood et al., assigned to the same assignee as the present application, and which is incorporated herein by reference in its entirety.

The system 40 includes an input unit 42 to receive images (in the form of image data), such as medical images from the image acquisition device (and related equipment) depicted in FIG. 1. The received images may be NMR, MRI, CT, ultrasound, x-ray, positron emission tomography (PET), or other types of images. The image data may be pre-organized into series and slices when it is received by the input unit 42. The image data may be received by the input unit 42 via any suitable data-transfer medium, including hardwire or wireless communication links or via portable storage media (such as CD, diskette, magnetic tape, and the like).

A line 44 represents communication between the various components of the system 40. The line 44 can be an actual bus or other connection, whether hardware or software. The system 40 includes or is otherwise coupled to one or more machine-readable storage media 46. The storage medium 46 can comprise a hard disk, database, server, or other mass data storage device that can store image data and/or one or more software programs 48. The stored image data can include the image data that is received by the input unit 42 and that is waiting for processing by the system 40. The stored image data can also include images that have been processed by the system 40 using rules, and that are to be provided as output.

The stored image data can include multiple series of slices, such as depicted in FIG. 2 above, in digital image format or other suitable electronic format. In one embodiment, the processed image data can be indexed in the storage medium 46 according to physician name, patient name, type of study (e.g., post-contrast series, pre-contrast series, subtraction series, and the like), series and slice identification numbers, dates of acquisition, acquisition technique used, body spatial location, and others. Based on this indexing system, the appropriate image data can be retrieved from the storage medium 46 by the system 40, and then sent to the appropriate receiving device for display.

The system 40 includes one or more processors 50. The processor 50 can comprise a digital signal processor (DSP) chip, an image processor, a microprocessor or microcontroller, or other type of processor capable to process image data. In one embodiment, processors having image processing capabilities similar to those used by current workstations may be implemented as the processor(s) 50, with the exception that the processor 50 also processes image data in accordance with one or more rules.

The processor 68 is coupled to the storage medium 46 to cooperate with the software 48 (or other machine-readable instruction) stored thereon. The software 48 can include an operating system to manage and control operation of the various components of the system 40. The software 48 can also include image-processing software that can apply parameters and criteria (including rules) to the received image data, calculate pixel intensities, compare calculated pixel intensities to known quantities, add color overlays to highlight tissue of interest, generate graphs and charts from the image data, calculate percent changes or time-dependent values, sort and classify image data, and other operations associated with processing image data.

One embodiment of the system 40 includes a rules list 52. The rules list 52 contains rules or other parameters by which received image data is to be processed. The rules list 52 may be stored in the storage medium 46 or in some other location in the system 40. Via use of the rules, images processed under different conditions and/or meeting different criteria can be provided to doctors on a case-specific basis.

The rules list 52 can include several of many rules that are available from existing literature or that are developed as medical research continues to validate new findings. An example of a "rule" is to search for and identify any pixels in the images which show an enhancement rate of at least 80% during the first time interval after the contrast agent is applied and/or where pixels show a washout rate of 5% over subsequent time intervals. The enhancement and washout rates to cause a pixel to be overlayed may be varied in the system 40 according to doctor preferences or based on the particular patient or tissue being examined-hence, the rules list 52 can include a wide range of selectable values that may be applied to images. Other rules can be programmed for time interval durations, types of images acquired, number of series and images involved, and other factors too numerous to detail herein, plus combinations thereof.

Additional examples of rules may be found in Christiane K. Kuhl et al., "DYNAMIC BREAST MR IMAGING: ARE SIGNAL INTENSITY TIME COURSE DATA USEFUL FOR DIFFERENTIAL DIAGNOSIS OF ENHANCING LESIONS?," Radiology, vol. 211, No. 1, April 1999, pp. 101-110; and in Nola M. Hylton, "VASCULARITY ASSESSMENT OF BREAST LESIONS WITH GADO-LINIUM-ENHANCED MR IMAGING," MRI Clinics of North America, vol. 9, No. 2, May 2002, pp. 321-331, with both of these articles being incorporated herein by reference in their entirety. The result of the rule being applied and identifying pixels of interest can be to provide coloring or other identification schemes that highlight tissues of interest and that classify (or otherwise links or sorts) images having similar characteristics. In one embodiment, the storage medium 46 can store color overlays. The color overlays can be overlaid over grey scale images, to highlight tissues of interest according to various color schemes. For example, tissue in some images that are extremely likely to be cancerous may be overlaid in red color, while less suspect tissue may be highlighted in blue color, as identified by the rules stored in the rules list 52. In some embodiments, the color is integrated into black and white images, rather than or in addition to being overlays. Example techniques that may be used by one embodiment of the present invention to provide colored images for purposes of analysis and diagnosis are disclosed in U.S. patent application Ser. No. 09/990,947, entitled "USER INTERFACE HAVING ANALYSIS STATUS INDICATORS," filed Nov. 21, 2001, assigned to the same assignee as the present application, and which is incorporated herein by reference in its entirety. An acceptable technique for selecting a region of interest, performing clustering, and then carrying out analysis on the pixels of the medical image data are described in co-pending U.S. patent application Ser. No. 09/722,063, entitled "DYNAMIC THRESHOLDING OF SEGMENTED DATA SETS AND DISPLAY OF SIMILARITY VALUES IN A SIMILARITY IMAGE," filed on Nov. 24, 2000, assigned to the same assignee of the present application, and which is incorporated herein by reference in its entirety. Also of interest is U.S. patent application Ser. No. 09/721,931, entitled "CONVOLUTION FILTERING OF SIMILARITY DATA FOR VISUAL DISPLAY OF ENHANCED IMAGE," filed on Nov. 24, 2000, and which is also assigned to the same assignee of the present application and incorporated herein by reference in its entirety. Any of the techniques disclosed by these applications may be implemented in conjunction with one or more rules in accordance with embodiments of the present invention. For the sake of brevity, the details disclosed in these co-pending applications are not repeated herein.

One embodiment of the system 40 may include baseline data 54 stored in the storage medium 46 or elsewhere. The baseline data 54 can include sample image data sets to which the specific rules are applied and later used as "models." The sample image data sets may include actual image data from patients that need processing, or it may comprise reference image data. For instance, if a certain doctor prefers to use post-contrast comprised of 3 series for his analysis with an enhancement rate threshold of 80%, then the 80%-rule is applied to an initial data set comprising 3 post-contrast series to "teach" the system 40 how to classify similar data sets in the future. Then, whenever any 3 post-contrast series particular for that doctor are subsequently provided to the input unit 42, the system 40 knows that the 80%-rule is to be applied to the new series.

Alternatively or in addition, the baseline data 54 can include data sets with which the processor 50 and software 48 compare image data processed according to a rule, so as to determine whether criteria for suspect tissue has been met, for example. As an illustration, the baseline data 54 can include graphical curves, images known to show cancerous tissue (identified by certain pixel intensity in grayscale), or other types of comparative data from a library of reference data. When one or more rules from the rules list 52 is applied to new image data, the results are compared with the baseline data 54 to determine how closely the results "fit" the baseline data (e.g., the closer the fit, the more likely the existence of cancer) or to determine some other conclusion.

Other types of baseline data 54 may be used in conjunction with or combined with the rules list 52. Such baseline data 54 would be familiar to those skilled in the art having the benefit of this disclosure, and so will not be described in detail herein. It is appreciated that in some instances, at least some of the rules from the rules list 52 and data from the baseline data 54 may be one and the same or otherwise share substantial overlap (e.g., the baseline data includes cancerous tissue depicted by pixels enhanced by 80% and the corresponding rules instruct the processor 50 and software 48 to identify pixels of newly received images that are enhanced by 80%).

The system 40 includes an output unit 56 to provide the output of the system 40 to one or more receiving devices. The output unit 56 symbolically represents image buffers, a network card, modem, or other components that are capable to provide processed images to receiving devices that display the images.

Figure 4:
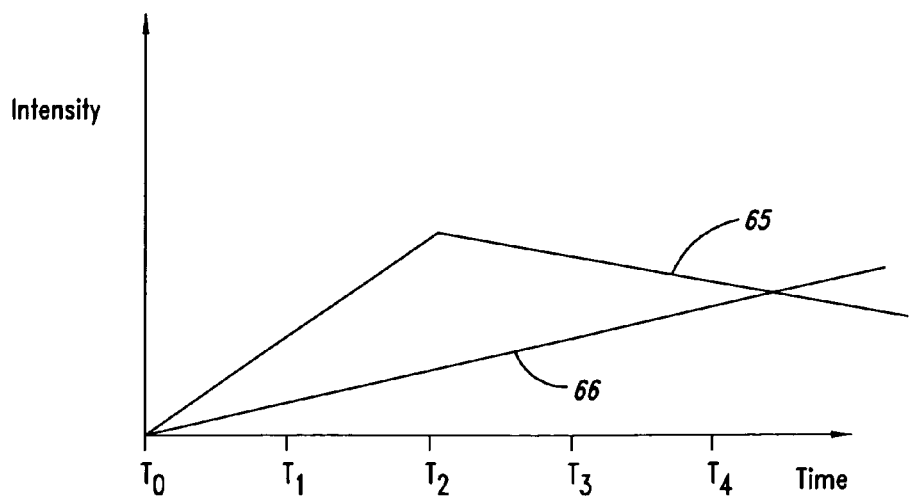
FIG. 4 shows time versus signal intensity curves that graphically depict tissue behavior in the presence of a contrast agent and with which one embodiment of the invention may be used.

FIG. 4 shows sample time versus signal intensity curves that graphically depict tissue behavior in the presence of a contrast agent and with which one embodiment of the invention may be used. The horizontal axis provides the time scale, which can be in minutes. The vertical axis provides an intensity scale (e.g., pixel intensity), which may be actual intensity, normalized intensity, percent change in intensity (as compared to pixel intensity in pre-contrast image), or other suitable scaling factor. The curves represent the intensity for one individual pixel in the image. This can be applied to group of pixels as well. The intensity at time to is the baseline measure before contrast agent is injected. At $t_1$ contrast agent is injected, at $t_2$, the first set of data post contrast is collected.

FIG. 4 shows two curves, curve 66 having an uptake value of above 70% and a washout rate of greater than 5% and curve 66 having an uptake rate of less than 70% and no washout. Curve 66 is indicative of healthy tissue, curve 65 may indicate a potential cancerous tumor that a physician must study more carefully, and all pixels having the characteristics of curve 66 will be highlighted to direct the physician to their location for further study.

Despite these generalities, however, different doctors may have different preferences as to the thresholds that may indicate healthy or unhealthy tissue. For example, some doctors may prefer to see an 85% enhancement (rather than an 80% enhancement) in the early post-contrast phase, before making a determination whether suspect tissue is present. Therefore, an embodiment of the invention provides the system 40 with capability to allow users to set their own limits and thresholds (e.g., rules) with regards to identification of pixel intensity for uptake and washout rates for the early, intermediate, and late post-contrast periods, and then have their images processed according to these rules, thereby resulting in presentation of images having highlighted tissues of interest that match these criteria.

FIG. 5 shows example rules that can be used by an embodiment of the invention, such as for the rules list 52. It is appreciated that the values and quantities shown in FIG. 5 are merely illustrative for purposes of demonstrating operation of an embodiment of the invention, and are not intended to be accurate representations of actual values and quantities. Moreover, the rules shown are not intended to be exhaustive of all possible rules—additions and variations are possible, including rules nested within rules.

The rules of FIG. 5 may be programmed for a particular doctor (such as "Doctor X" in this example). Once the particular doctor's rules have been programmed into the system 40, the rules can be subsequently applied to all of that doctor's patients and need not be reprogrammed, unless modifications or additions are desired. Different rules may be programmed for each and every doctor, and one doctor may use other doctor's rules for comparative or other purposes, if desired. Alternatively or in addition, there may be identifiers 69 for institution (e.g., "Hospital W") and 71 for type of study (e.g., contrast study), which may be used to correlate the rules to baseline data or to received image data.

In the example of FIG. 5, a first set of rules 68 specify the number of pre- and post-contrast series that are acquired for the doctor and received by the system 40 for processing. In this example, Doctor X prefers to use/acquire 3 pre-contrast series and 4 post-contrast series (which may be numbered series #1-#7, respectively). If one or more subtraction series are desired by Doctor X, then rules 70 may specify which series the subtraction series are to be obtained, which in this case are series #4 minus series #1 and series #5 minus series #2.

From the image data that is received by the system 40, rules 72 can state: "identify pixels from the images that have this uptake rate (enhancement rate) during this uptake interval, and having this washout rate." The respective values 85%±3%, 1.1 minutes±0.5 minutes, and 7%±2% may then be programmed into the rules list 52 for Doctor X.

The rules 74 may relate to a parametric series or other series where tissues of interest are highlighted in color. For instance, the rules 74 may be nested within the rules 72, so as to generate rules to the effect: "For pixels from rule 72 that meet the enhancement rates of 88% and above during the specified time interval and having the specified washout rate, color them in red to indicate malignant tissue" and "For pixels from rule 72 that meet the enhancement rates of 82%-87% during the specified time interval and having less than the specified washout rate, color them in blue to indicate suspect tissue." In other embodiments, tissues of interest meeting the defined parameters need not necessarily be definitively classified as malignant or suspect, but rather as tissue requiring further investigation by Doctor X.

A rule 76 may allow Doctor X to specify which slices from which series he wants to have linked to indicate that they are spatially aligned. For example, Doctor X may prefer only aligned images from the pre-contrast series #1-#3 and the post-contrast series #4-#5 as worthy of viewing in relationship to each other-the other images from the other series are preferred to be viewed on an as-needed basis. Therefore, the rules 76 specify a linking of aligned slices from series #1-#5, which causes these images to be grouped together by the system 40 and retrievable for display as a group on Doctor X's display terminal.

Thus, in one embodiment, the image data processing performed by the processor 50, in cooperation with the software 48 and the applicable rule(s) from the rules list 52, includes processing the images to calculate (or otherwise generate from the received image data) a subtraction series, parametric series (where color may be added to highlight tissues of interest), maximum intensity projection series, reformatted series, or other series and combinations thereof, and send them to the appropriate terminal(s) for review by a doctor. Such processing may be used in conjunction with contrast studies, and it is understood that other embodiments of the invention may have application towards non-contrast image analysis.

In one embodiment of the system 40, baseline data 54 may be provided as either or both: a) sample data set on which the specific rules are applied in order to generate results that are used as a "model" for similar future image data; or b) a library of known results with which new results are compared in order to arrive at a conclusion. FIG. 6 shows sample baseline data for Doctor X, and again, is understood to be merely illustrative and not necessarily representing actual values/quantities.

The baseline data can include patient ID data 78 for Doctor X. The patient ID data 78 can comprise a list of all of Doctor X's patients, for instance, such that when acquired images in Digital Imaging and Communications in Medicine (DICOM) format are received having such ID data, the system 40 knows that these images belong to Doctor X's patients and can thus apply Doctor X's pre-programmed rules to them.

The baseline data can include sample image and series data 80, such as image #7 from series #8 or image #12 from series #3, as identified in FIG. 6. By referencing or including these images, the data 80 provides system 40 with images on which rules may be applied to obtain conclusions that may be used as comparative models for future images.

Alternatively of in addition, the baseline data may include a library 82 of validated results. For example, known cancerous tissue from this patient may have pixel uptake intensity changes of 80-100%, suspect tissue in the range of 60-79%, and normal tissue in the range of 0-59%. When Doctor X's rules are applied to the received image data and the pixel intensities are calculated therefrom, the calculated pixel intensities may be compared with the data from the library 82 to conclude whether the tissue now under study is cancerous, suspect, or normal. In this example, empirical data from known tissue is used to modify the rules to provide a more accurate prediction of tissue being tested. Of course, Doctor X is free to accept, reject, or further investigate these conclusions generated by the system 40 by further study of the highlighted areas.

The various rules and baseline data depicted in FIGS. 5-6 can be programmed into the system 40 via any suitable administrative interface, including web-based interfaces. The co-pending application entitled "SYSTEM AND METHOD FOR DISTRIBUTING CENTRALLY LOCATED PRE-PROCESSED MEDICAL IMAGE DATA TO REMOTE TERMINALS," identified above, discloses example screen shots of administrative interfaces that may be used to configure the system 40 according to various embodiments of the invention. Some of these administrative interfaces may be used to program or modify rules and baseline data, alternatively or in addition to what is shown in FIGS. 5-6.

Figure 7A:
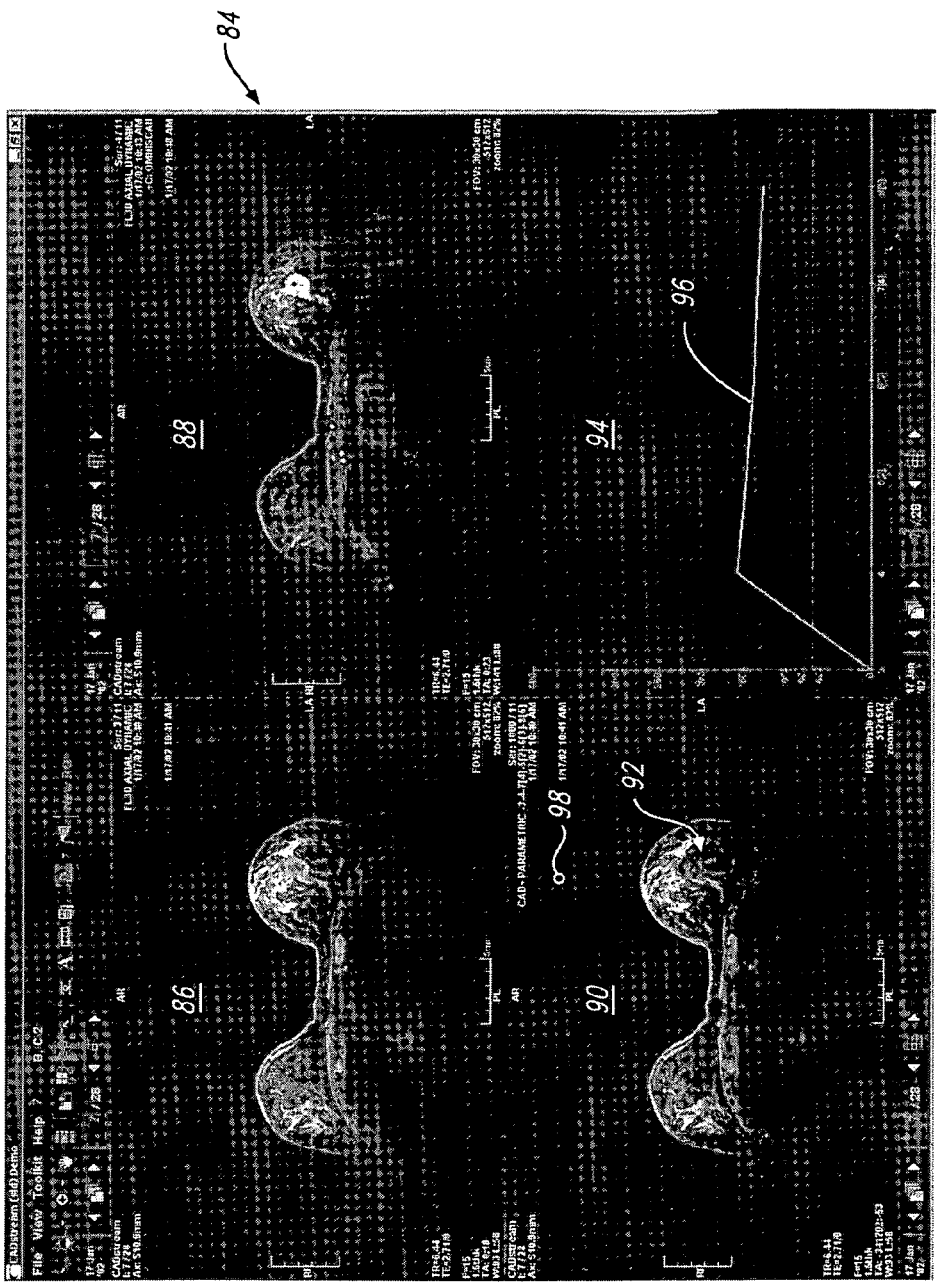
FIGS. 7A-7C show example user interfaces for displaying images that have been processed with the rules-based system of FIG. 3 according one embodiment of the present invention, with graphs.

FIG. 7A shows an example user interface for displaying images that have been processed with the rules-based system of FIG. 3 according one embodiment of the present invention. It is appreciated that the depicted user interface is merely illustrative, and that the images shown thereon have not necessarily been processed according to the specifically illustrated example rules and baseline data depicted in FIGS. 5-6. Moreover, other embodiments can provide user interfaces with different layouts, informational displays, controls, displayed images, and the like.

The user interface includes a display area 84 having one or more medical images 86, 88, and 90 shown thereon. The medical images 86-90 can be pre-processed images stored in the storage medium 46, which were processed and sorted by the system 42 according to programmed parameters, such as from the rules list 52 and/or the baseline data 54. The medical images 86-90 are shown as examples for illustrating examination for breast cancer and a study of whether or not the cancer has metastasized and spread to other tissues within the patient. Of course, other embodiments of the invention are applicable to all sorts of medical images of different parts of the body or to images that are not necessarily medical in nature. One embodiment of the invention may be particularly beneficial for brain image data, lymph node image data, or many other types of tissue that are susceptible to cancers or other diseases that spread to different locations within the body, including studies where contrast agents are applied.

The medical images 86-90 may be organized according to the series and slice scheme depicted in FIG. 2. Color may be present in one or more of the medical images 86-90 to highlight potential tissues of interest, such as colored regions 92 in the medical image 90 (e.g., in an image from a parametric series). The medical image 86 may be considered as a pre-contrast image, while the medical images 88 and 90 may be post-contrast images.

In one embodiment, the display area 84 can present a window 94 having a chart with a curve 96 (or other graphical data) shown therein. In this example, the curve 96 depicts % change in pixel intensity (vertical axis) versus time (horizontal axis) similar to the graph at FIGS. 4A and 4B. The % percent change is compared using the pre-contrast image 86 as the baseline.

In operation, a cursor 98 or other navigation element may be positioned over any of the pixels of the medical images 88 or 90, and the corresponding curve 96 is generated in the window 94 that tracks the % percent change in intensity over a period of time for the selected pixels that match the rules.

The time $t_0$ is shown as number 3, $t_2$ as 4, $t_3$ as 5, etc. The preconstrast series used was series 3 and the post contrast series were series 4, 5, 6, 7 and 8, taken as regular time intervals $t_2$-$t_6$. The tissue that corresponds to this pixel intensity change is highlighted at 92 in the image. This provides a location for further study, even if only a few pixels exhibit this behavior. Tissue that may have been difficult or impossible to detect can now be seen and studied.

Assume for example, that this particular doctor has chosen 80% (or more) enhancement during a 1 minute interval and 20% (or more) washout as the baseline data for identifying cancerous or suspect tissue. Assume further that the doctor has instructed that cancerous tissue (classified according to the chosen parameters) be colored in red and suspect tissue be colored in green. Therefore, the system 40 classifies, processes, and sorts this doctor's image data to produce the results shown in FIG. 7A. For example, the parametric image 90 was generated with regions 92 showing red and green colors that match the preprogrammed rules for uptake and washout rates (e.g., approximately 80% enhancement and 20% washout).

Figure 7B:
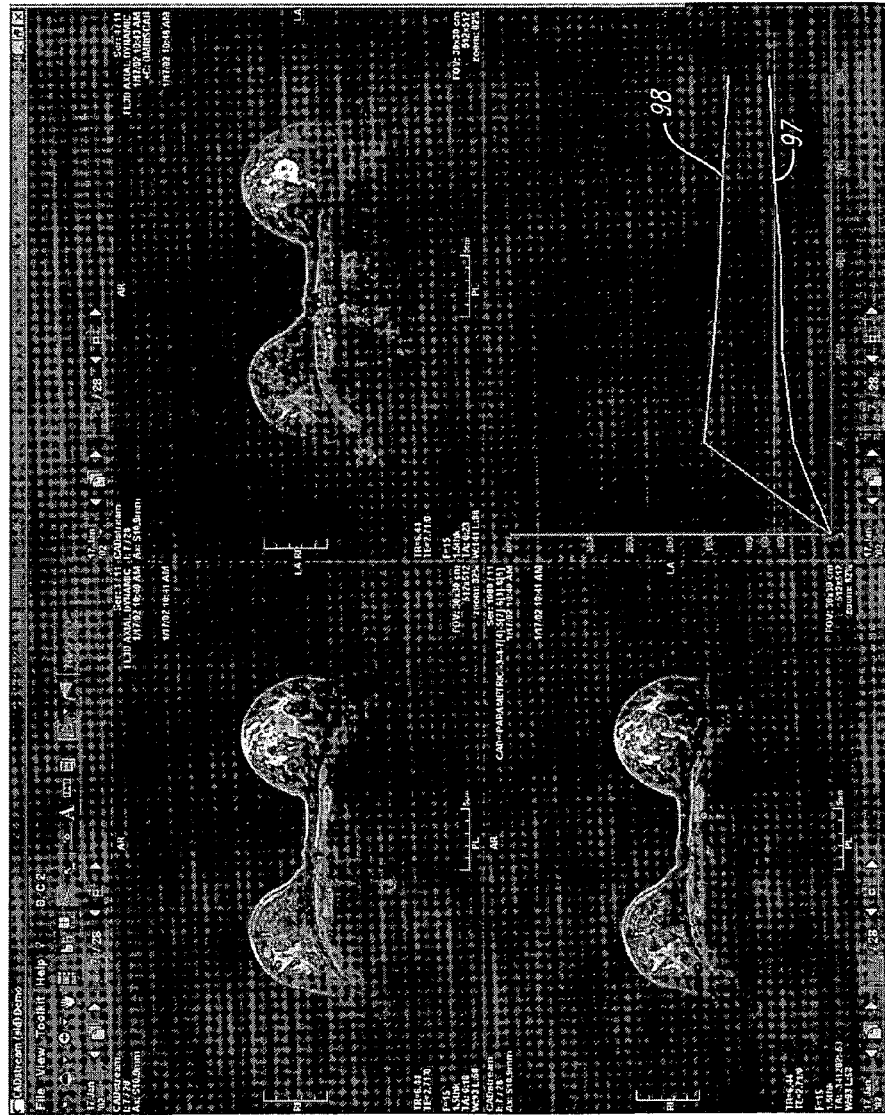
Figure 7C:
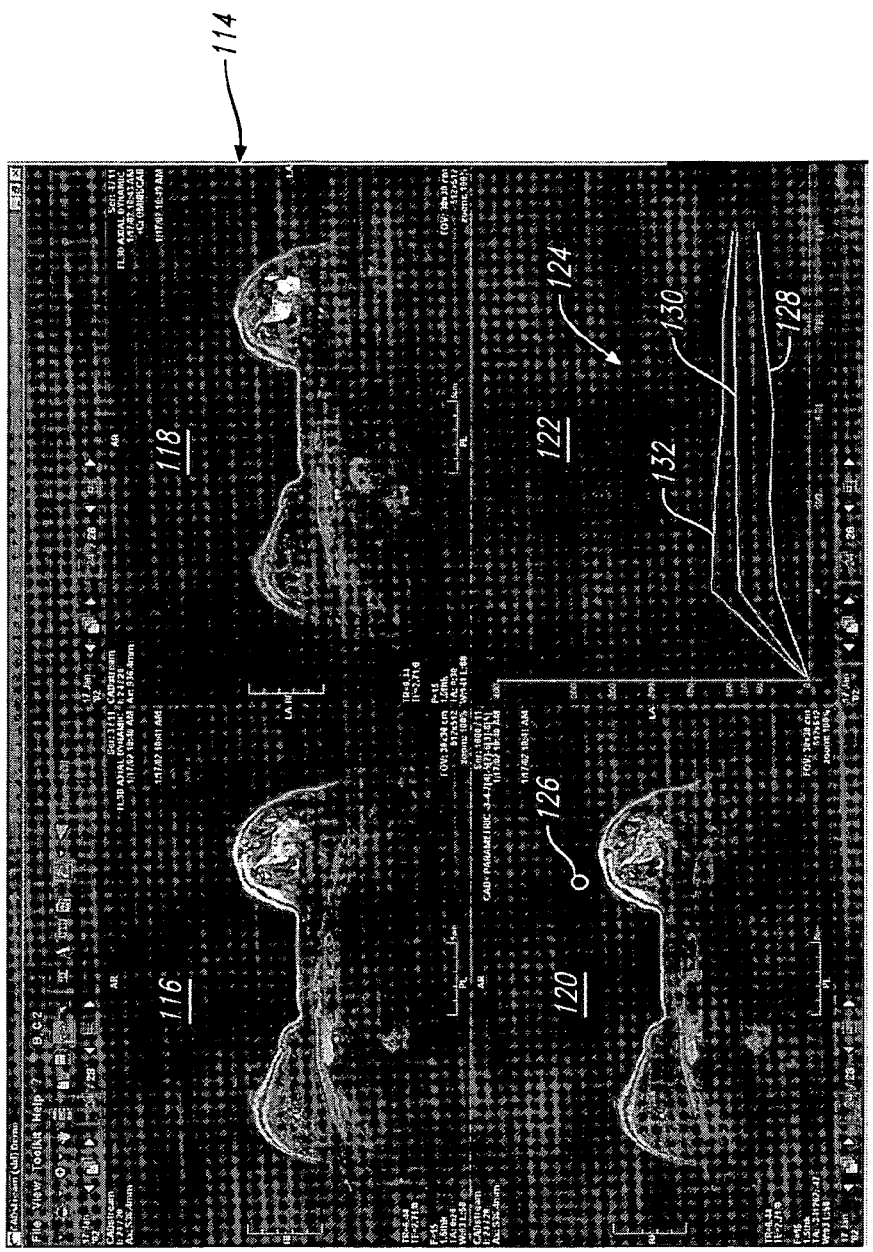

FIG. 7B shows the same images 90 as FIG. 7A, but a curve 97 is shown for pixels that did not meet the established rule and thus are not highlighted. FIG. 7C illustrates images 116-120 from the same patient, but at different slices in the body, showing two sets of pixels at lines 130 and 132 (in a chart 124 in a window 122) that meet the rule and thus corresponding pixels are highlighted in the image 120—a selection cursor 126 may be used by the physician to specifically select/focus on pixels. Curve 98 in FIG. 7B and curve 132 (or 130) in FIG. 7C are more indicative of a malignant tumor, so the pixels that correspond to these curves will be highlighted for the physician and studied more carefully.

Figure 8:
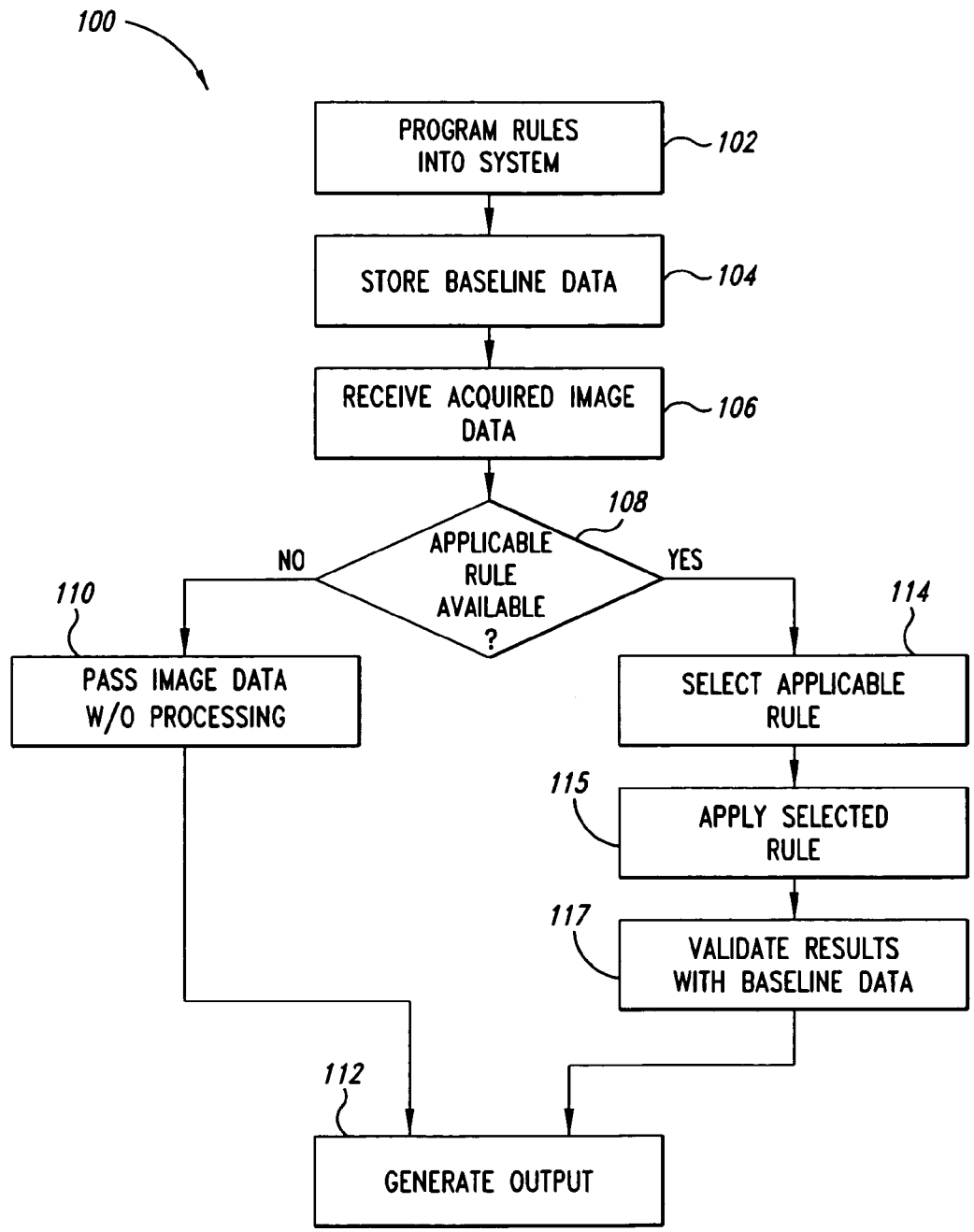
FIG. 8 is a flowchart illustrating a method for applying rules to process images for display according to one embodiment of the present invention.

FIG. 8 is a flowchart 100 illustrating a method for applying rules(s) to process images for display according to one embodiment of the present invention. At least some of the elements of the flowchart 100 may be embodied in machine-readable instructions stored on a machine-readable medium, such as the software 48 on the storage medium 46. It is appreciated that at least some of the elements of the flowchart 100 can be combined operations, rather than discrete operations, and that the operations need not necessarily occur in the exact order shown.

At a block 102, the system 40 receives or is programmed with rules, such as those depicted in FIG. 5 and described throughout this specification. A plurality of different (or overlapping) rules may be provided based on institution, doctor, patient, study, or other classification or hierarchy. The programmed rules may be entered via user interfaces and then stored as the rules list 52. Previously programmed rules may also be modified at the block 102, such as when a doctor decides to change existing rules due to the nature of the patient or due to the type of image data that is available.

At a block 104, baseline data 54 may be stored or otherwise provided to the system 40. As described above, the baseline data 54 can include data to be used for comparative purposes or for purposes of "teaching" the system 40 how to process future similar data.

At a block 106, acquired image data (such as from the imaging device of FIG. 1) is received by the system 40 for processing. In one embodiment, the received image data is in DICOM format and organized into series and slices as shown in FIG. 2. The received image data may have identifiers associated with it, such as doctor ID, number of series and slices per series, patient ID, or other identification data that can be used by the system 40 to correlate the received image data with the appropriate rule(s).

At a block 108, the system 40 determines whether there are one or more rules that may be applied to the received image data. As an example, Doctor X's rules may be tailored for images from 3 pre-contrast series and 4 post-contrast series. However, if the system 40 receives 5 post-contrast series that correlate or is otherwise identified to Doctor X, this does not fit into Doctor X's rules. Therefore, at a block 110, the system 40 passes the received non-matching image data without processing, and an output generated a block 112 includes the non-processed images (with perhaps an indicator to notify Doctor X that the images were not processed). The operation at the block 110 thus serves as a safety feature to prevent the system 40 from "guessing" and erroneously processing non-conforming data.

If at the block 108, however, it is determined that there is an applicable rule that is available (e.g., the received image data can be identified to a doctor and conform in number, type, content, etc. to the rules for that doctor), then that applicable rule(s) is selected at a block 114. The applicable rule is applied to the corresponding image data at a block 115. This includes highlighting images with color, identifying pixels having certain intensities, generating new series and images from the received images, and other processing operations described above and others. It is appreciated that multiple rules and application thereof may be performed at the block 115, including nested rules where application of a rule is dependent on or concurrent with application of another rule.

The applicable rule will, in many embodiments be a default set of rules pre-stored in the memory and not identified with any particular doctor. These rules can be installed by the maker of the equipment, or the hospital, or some other knowledge provider based on previously created suitable rules that apply to most cases.

If baseline data is present for comparative purposes, some of the results of the rule application of the block 115 may be validated at a block 117. For example, if the rules identified certain pixels meeting defined intensity levels, the validation at the block 117 can suggest conclusions as to whether cancerous or suspect tissue is present based on the results of the comparison with the baseline data. The results representing the processed image data are then generated as output at the block 112, which may appear as images similar to the screen shots of FIGS. 7A-7C.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various equivalent modifications are possible within the scope of the invention and can be made without deviating from the spirit and scope of the invention.

For instance, the image under study can be any acceptable image for which a detailed investigation is to be performed by comparing images of the same object to each other or images of one object to images of another object. In one embodiment, the object under study is human tissue and the region of interest corresponds to cells within the human body having a disease or particular impairment, such as cancer, Alzheimer's, epilepsy, or some other tissue that has been infected with a disease. Alternatively or in addition, the region of interest may be certain types of tissue that correspond to body organs, muscle types or certain types of cells for which an analysis or investigation is desired. As a further alternative or addition, the object under investigation may be any physical object, such as an apple, bottles of wine, timber to be studied, or other detailed object for which an analysis is to be performed and a search made for similar regions of interest within the object itself, or for one object to another.

These and other modifications can be made to the invention in light of the above detailed description. The terms used in the following claims should not be construed to limit the invention to the specific embodiments disclosed in the specification and the claims. Rather, the scope of the invention is to be determined entirely by the following claims, which are to be construed in accordance with established doctrines of claim interpretation.

What is claimed is:

1. A system for processing medical images of human tissue under study comprising:
   a first memory storing a plurality of sets of images of locations representative of tissue with a patient under study;
   a first set of said plurality of the sets of images representing tissue prior to injection of a contrast agent;
   a second set of said plurality of the sets of images representing tissue at a selected time after injection of a contrast agent;
   a second memory storing a plurality of rules to be applied to said images;
   a computer-aided detection processor configured to apply the set of rules to the first and second sets of images to thereby detect tissues of interest, the processor further configured to classify the tissues of interest into a first class of lesions if those tissues of interest have a first characteristic defined by the set of rules and to classify the tissues of interest into a second class of lesions if those tissues of interest have a second characteristic defined by the set of rules; and
   a visual display having an image from said plurality of sets of images displayed thereon, the image having a first indicia thereon of the detected tissues of interest classified into the first class of lesions and having a second indicia thereon of the detected tissues of interest classified into the second class of lesions.

2. The system according to claim 1 wherein the second memory is programmable to receive and store therein user selected rules.

3. The system of claim 1 wherein the visual display is a color display and the first and second indicia highlights in a separate color the detected tissues of interest in the first and second classes of lesions, respectively.

4. The system of claim 1, further including a third set of said plurality of the sets of images, the third set representing tissue at a second selected time after injection of the contrast agent.

5. An article of manufacture, comprising:
   a machine-readable medium having instructions stored thereon to:
   select at least one rule, from among a plurality of available rules, that is applicable to medical image data;
   cause a computer-aided detection processor to process the medical image data according to the selected rule to thereby detect tissues of interest;
   classify the tissues of interest into a first class of lesions if those tissues of interest have a first characteristic defined by the selected rule and to classify the tissues of interest into a second class of lesions if those tissues of interest have a second characteristic defined by the selected rule;
   generate an output representative of the processed medical image data, the output having a first indicia of the detected tissues of interest classified into the first class of lesions and having a second indicia of the detected tissues of interest classified into the second class of lesions; and
   automatically process subsequent similar medical image data according to that same selected rule and other medical image data according to its respective applicable rule.

6. The article of manufacture of claim 5 wherein the medical image data includes a medical image of tissue enhanced with a contrast agent.

7. The article of manufacture of claim 5 wherein the machine-readable medium further includes instructions stored thereon to:
   determine if no rule is available that is applicable to the medical image data; and
   generate the output representative of the medical image data, unprocessed, if it is determined that no applicable rule is available for that medical image data.

8. The article of manufacture of claim 5 wherein the instructions to process the medical image data include at least one of instructions to:
   add color to the medical image data to highlight the detected tissues of interest;

generate new image data from at least some of the medical image data;

link images having image data that is spatially related; and generate graphical information as part of the generated output.

9. The article of manufacture of claim 5 wherein the machine-readable medium further includes instructions stored thereon to include new rules added to the available rules, including modifications thereof.

10. A system, comprising:

means for receiving image data;

means for selecting at least one rule, from among a plurality of available rules, that is applicable to the received image data;

means for processing the received image data according to the selected rule to thereby classify tissues of interest into a first class of lesions if those tissues of interest have a first characteristic defined by the selected rule and to classify the tissues of interest into a second class of lesions if those tissues of interest have a second characteristic defined by the selected rule; and means for generating an output representative of the processed image data, the output having a first indicia of the detected tissues of interest classified into the first class of lesions and having a second indicia of the detected tissues of interest classified into the second class of lesions.

11. The system of claim 10 wherein the means for selecting at least one rule that is applicable to the received image data include a means for comparing an identifier associated with that rule to an identifier associated with the image data.

12. The system of claim 10 wherein the image data comprises DICOM format medical image data of tissue enhanced by a contrast agent.

13. The system of claim 10, further comprising a means for acquiring the image data.

14. An apparatus, comprising:

a storage medium to store a software program adapted to operate in conjunction with a plurality of rules that specify how received medical images are to be processed; and a processor coupled to the storage medium to cooperate with the software program to select at least one of the rules and to process the received medical images based on the selected rule and to process similar received medical images, for which the selected rule applies, according to that selected rule, and further to process other received medical images according to other rules, the processor being configured by the software program to classify the tissues of interest into a first class of lesions if those tissues of interest have a first characteristic defined by the selected rule and to classify the tissues of interest into a second class of lesions if those tissues of interest have a second characteristic defined by the selected rule to thereby generate an output representative of the processed medical image data, the outout having a first indicia of the detected tissues of interest classified into the first class of lesions and having a second indicia of the detected tissues of interest classified into the second class of lesions.

15. The apparatus of claim 14 wherein the selected rule includes criteria by which pixel intensity representative of contrast agent uptake and washout are to be identified.

16. The apparatus of claim 14 wherein the software program provides an interface through which rules and modifications thereof can be stored in the storage medium.

17. The apparatus of claim 14 wherein the software program includes code to not process the received image data if no available rule is applicable to the received image data.

18. A method, comprising:

receiving image data;

selecting at least one rule, from among a plurality of available rules, that is applicable to the received image data;

using a computer-aided detection processor to process the received image data according to the selected rule and thereby detect tissues of interest, the processor being configured to classify the tissues of interest into a first class of lesions if those tissues of interest have a first characteristic defined by the selected rule and to classify the tissues of interest into a second class of lesions if those tissues of interest have a second characteristic defined by the selected rule;

generating an output representative of the processed image data, the output having a first indicia of the detected tissues of interest classified into the first class of lesions and having a second indicia of the detected tissues of interest classified into the second class of lesions; and automatically processing subsequently received and similar image data according to that same selected rule.

19. The method of claim 18 wherein the received image data includes medical images of human tissue.

20. The method of claim 19 wherein the medical images include magnetic resonance (MR) images.

21. The method of claim 20 wherein the MR images are enhanced with a contrast agent.

22. The method of claim 21 wherein at least some of the available rules relate to pixel enhancement during uptake of the contrast agent and during washout of the contrast agent.

23. The method of claim 18 wherein selecting the rule that is applicable to the received image data is based on preferences of a person associated with both the rule and with the received image data.

24. The method of claim 18 wherein if no rule is available that is applicable to the received image data, the method further comprising generating the output representative of the received image data without processing by the computer-aided detection processor.

25. The method of claim 18, further comprising:

receiving baseline data;

applying one of the rules to the baseline data; and automatically applying that rule to received image data that is similar to the baseline data.

26. The method of claim 18, further comprising:

receiving baseline data; and comparing the processed image data with the baseline data to determine a conclusion related to the processed image data.

27. The method of claim 18 wherein processing the received image data according to the selected rule includes at least one of adding color to the received image data to highlight tissue of interest, generating new image data from at least some of the received image data, linking images having image data that is spatially related, and generating graphical information as part of the generated output.

28. The method of claim 18, further comprising applying at least one additional rule to the image data that has been previously processed with the selected rule.

29. The method of claim 18, further comprising:
combining selected ones of the available rules to create compound rules; and
using the compound rules to generate new image data and generating the output from the new image data.

30. The system of claim 1, further comprising a computer-aided diagnosis processor configured to analyze the detected tissues of interest to determine if any of the detected tissues of interest are likely a malignant tumor.

31. The system of claim 30 wherein the computer-aided detection processor is further configured to function as the computer-aided diagnosis processor.

32. The system of claim 30 wherein the visual display displays the image having the first indicia indicating that a selected one of the detected tissues of interest in the first class of lesions is likely a malignant tumor.

33. The system of claim 32 wherein the visual display is a color display and displays the selected one of the detected tissues of interest that is likely a malignant tumor in a color different from a color used to display the image.

34. The system of claim 32 wherein the visual display is a color display and displays detected tissues of interest in a first color and displays the selected one of the detected tissues of interest that is likely a malignant tumor in a second color different from the first color.

35. The method of claim 18 wherein generating the output comprises displaying an image indicating the detected tissues of interest.

36. The method of claim 18, further comprising using a computer-aided diagnosis processor to analyze the detected tissues of interest to determine if any of the detected tissues of interest are likely a malignant tumor.

37. The method of claim 36 wherein generating the output comprises displaying an image indicating that a selected one of the detected tissues of interest is likely a malignant tumor.

38. The method of claim 37 wherein generating the output comprises displaying an image having a first indicia indicating that the selected one of the detected tissues of interest is in the first class of lesions and is likely a malignant tumor.

39. The method of claim 37 wherein generating the output comprises displaying a color image indicating the selected one of the detected tissues of interest that is likely a malignant tumor in a color different from a color used to display the image.

40. The method of claim 37 wherein generating the output comprises displaying a color image that displays detected tissues of interest in a first color and displays the selected one of the detected tissues of interest that is likely a malignant tumor in a second color different from the first color.

41. An article of manufacture, comprising;
a machine-readable medium having instructions stored thereon to:
select at least one rule, from among a plurality of available rules, that is applicable to medical image data;
cause a computer-aided detection processor to process the medical image data according to the selected rule to thereby detect tissues of interest;
add color to the medical image data to highlight the detected tissues of interest;
generate an output representative of the processed medical image data;
generate new image data from at least some of the medical image data;
link images having image data that is spatially related; and
automatically process subsequent similar medical image data according to that same selected rule and other medical image data according to its respective applicable rule.

* * * * *